United States Patent
Weber et al.

(10) Patent No.: US 10,111,454 B2
(45) Date of Patent: *Oct. 30, 2018

(54) RANGE OF ASEPTICALLY PRODUCED INFANT FOODS HAVING LOW CONCENTRATIONS OF UNDESIRED BY-PRODUCTS AND METHODS FOR MAKING SAME

(71) Applicant: NESTEC S.A., Vevey (CH)

(72) Inventors: Frank Weber, Eschborn (DE); Simon Alexander Hutschenreuter, Grand Rapids, MI (US); Nadine Knoeller, Zimmern O.R. (DE); Martinas Kuslys, Grosshochstetten (CH)

(73) Assignee: Nestec, S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/153,121

(22) Filed: May 12, 2016

(65) Prior Publication Data

US 2016/0262436 A1 Sep. 15, 2016

Related U.S. Application Data

(62) Division of application No. 12/672,911, filed as application No. PCT/EP2008/007263 on Sep. 5, 2008, now abandoned.

(30) Foreign Application Priority Data

Sep. 7, 2007 (EP) .................................... 07017565

(51) Int. Cl.
| | |
|---|---|
| A23L 5/20 | (2016.01) |
| A23L 19/00 | (2016.01) |
| A23L 33/00 | (2016.01) |
| A23L 1/015 | (2006.01) |
| A23L 1/212 | (2006.01) |
| A23L 1/29 | (2006.01) |

(52) U.S. Cl.
CPC .............. *A23L 5/21* (2016.08); *A23L 1/0151* (2013.01); *A23L 1/2128* (2013.01); *A23L 1/296* (2013.01); *A23L 19/09* (2016.08); *A23L 33/40* (2016.08); *A23V 2002/00* (2013.01)

(58) Field of Classification Search
CPC ....... A23B 4/005; A23L 1/212; A23L 1/2128; A23L 3/00

USPC ................................................. 426/531, 615
See application file for complete search history.

(56) References Cited

U.S. PATENT DOCUMENTS

| | | | |
|---|---|---|---|
| 6,190,724 B1 | 2/2001 | Sawatzki | |
| 2005/0095324 A1* | 5/2005 | Santana Suarez | ..... B65D 77/08 |
| | | | 426/119 |
| 2006/0019017 A1 | 1/2006 | Singh | |
| 2006/0105095 A1* | 5/2006 | Anthony | ................... A23L 3/36 |
| | | | 426/615 |
| 2006/0210692 A1* | 9/2006 | Mower | .................... A61K 8/29 |
| | | | 426/618 |
| 2011/0183062 A1 | 7/2011 | Ursel | |
| 2011/0287161 A1 | 11/2011 | Weber | |

FOREIGN PATENT DOCUMENTS

JP  2010537649  12/2010

OTHER PUBLICATIONS

U.S. Appl. No. 12/672,913, filed Feb. 10, 2010.*
XP002494035. Kuballa, Thomas. Prior Art in German—"Furan in Kaffeee und Anderren Lebensmitteln." Journal of Consumer Protection and Food Safety. pp. 429-433. 2007.
XP002494034. Yoshida, Izumi. "Rapid and Improved Determination of Furan in Baby Foods and Infant Formulas by Headspace GC/MS." J. Food Hyg. Soc. Japan. vol. 48. No. 4. pp. 83-89. Aug. 2007.
XP002494033. Bianchi, Federica. "Development and Validation of a Solid Phase Micro-extraction-gas Chromatography-mass Spectrometry Method for the Determination of Furan in Baby-food." Journal of Chromatography A. pp. 268-272. 2006.
International Search Report and Written Opinion dated Oct. 27, 2008 received in corresponding PCT Application No. PCT/IEP2008/007263.
"Heatprocessing". BusinessDictionary.com. pp. 1 of 1. 2010.
"Feeding Infants, A Guide for Use in the Child Nutrition Programs." United States Department of Agriculture Food and Nutrition Service. Dec. 2001. pp. 43-59.

* cited by examiner

*Primary Examiner* — Ruth A Davis
(74) *Attorney, Agent, or Firm* — Gary M. Lobel, Esq.

(57) ABSTRACT

A range of infant food products wherein each product in the range includes minimal levels of undesired by-products produced during processing as indicated by less than about 15 micrograms furan per kg food product. Methods of production and use thereof are also disclosed.

17 Claims, 6 Drawing Sheets

RANGE OF ASEPTICALLY PRODUCED INFANT FOODS HAVING LOW CONCENTRATIONS OF UNDESIRED BY-PRODUCTS AND METHODS FOR MAKING SAME

CROSS REFERENCE TO RELATED APPLICATIONS/INCORPORATION BY REFERENCE STATEMENT

This application is a division of U.S. Ser. No. 12/672,911, filed Jul. 13, 2010; which is a national stage application filed under 35 USC § 371 of App No. PCT/EP2008/007263, filed Sep. 5, 2008; which claims priority to EPO Serial No. 07017565.8, filed Sep. 7, 2007. The entire contents of the above-referenced patent applications are hereby expressly incorporated herein by reference.

BACKGROUND

1. Field of the Invention

The presently disclosed and/or claimed inventive concept(s) relates generally to infant food products and particularly to infant food products having low concentrations of undesired by-products produced during processing or packaging.

2. Description of Related Art

It is known that processing of food products can produce undesirable by-products. For example, when food products are roasted, the roasting process can lead to the production of undesirable acrylamide. Alternatively, when food products are subjected to cooking, for example in cans and jars, this can lead to production of undesirable furan.

Furan, like acrylamide, is a substance which is generated naturally during the heating of food products during processing. It is not a synthetic substance added to the food as an ingredient, but occurs in food products as a result of processing.

High concentrations of furan have been shown to be genotoxic and in animal experiments carcinogenic.

Furan is listed in the Department of Health and Human Services list of carcinogens, and considered as possibly carcinogenic by the International Agency for Research on Cancer, based on studies in the laboratory animals at high exposures. Thus, high concentrations of furan are undesirable in food products.

Furan can be generated by heat processing of foods comprising polyunsaturated fatty acids (PUFAs), ascorbic acid (vitamin C), β-carotene, sugars and amino acids.

BRIEF DESCRIPTION OF THE DRAWINGS

In FIG. 5 the results are shown with regard to a vegetable food product comprising carrot. In FIG. 6 the results are shown with regard to a savoury food product comprising cod and mixed vegetables.

DETAILED DESCRIPTION

Definitions

Within the context of this specification, the term "about" means plus or minus 20%, such as (but not limited to) plus or minus 10%, or plus or minus 5%, or plus or minus 2%.

The term "range of infant food products" refers to a plurality of packaged nutritional compositions (e.g. 2 or more) that, together with milk, provide the nutritional requirements an infant. The range could be interpreted to form a kit of parts.

The term "by-product" refers to a substance present in a food product that is produced during processing of the product.

There are recognized stages of infant development that can be defined, wherein Stage 1 refers to about 4 to about 6 months of age; Stage 2 refers to about 6 to about 8 months of age, Stage 3 refers to about 8 to about 12 months of age, and Stage 4 (also referred to as Junior Stage) refers to about 12 to about 36 months of age. Infants falling within these different developmental stages have different nutritional requirements.

The presently disclosed and/or claimed inventive concept(s) is not limited to the particular methodology, protocols, and reagents described herein because they may vary. Further, the terminology used herein is for the purpose of describing particular embodiments only and is not intended to limit the scope of the presently disclosed and/or claimed inventive concept(s). As used herein and in the appended claims, the singular forms "a," "an," and "the" include plural reference unless the context clearly dictates otherwise.

Unless defined otherwise, all technical and scientific terms and any acronyms used herein have the same meanings as commonly understood by one of ordinary skill in the art in the field of the presently disclosed and/or claimed inventive concept(s). Although any methods and materials similar or equivalent to those described herein can be used in the practice of the presently disclosed and/or claimed inventive concept(s), particular non-limiting methods, devices, and materials are described herein.

All patents, patent applications, and publications mentioned herein are incorporated herein by reference to the extent allowed by law for the purpose of describing and disclosing the compounds and methodologies reported therein that might be used with the presently disclosed and/or claimed inventive concept(s). However, nothing herein is to be construed as an admission that the presently disclosed and/or claimed inventive concept(s) is not entitled to antedate such disclosure by virtue of prior presently disclosed and/or claimed inventive concept(s).

All percentages for weights expressed herein are by weight of the total food product unless specifically stated otherwise.

Within this specification embodiments have been described in a way which enables a clear and concise specification to be written, but it is intended and will be appreciated that embodiments may be variously combined or separated without parting from the presently disclosed and/or claimed inventive concept(s)

The Presently Disclosed and/or Claimed Inventive Concept(s)

It is, therefore, an object of the presently disclosed and/or claimed inventive concept(s) to provide a new range of infant food products that includes a reduced level of undesirable by-products. The level of undesirable by-products can be measured, for example, by reference to furan concentration in a food product.

These and other objects are addressed in one aspect of the presently disclosed and/or claimed inventive concept(s) by providing a range of infant food products wherein each product in the range has less than about 15 micrograms furan per kg food product. The resulting range of infant food products has the advantage that each food product in the range has minimal concentrations of undesirable by products produced during processing. In various embodiments, the components include substantially no furan (e.g. less than about 5 micrograms/kg furan in the food product) or no furan.

In a further aspect, the presently disclosed and/or claimed inventive concept(s) provides a feeding regime for meeting the nutritional needs of an infant during different stages of development, the regime comprising administering to an infant a range of food products according to the presently disclosed and/or claimed inventive concept(s).

In a further aspect, the presently disclosed and/or claimed inventive concept(s) provides use of a range of food products according to the presently disclosed and/or claimed inventive concept(s) in the manufacture of one or more medicaments for the prevention or treatment of a nutritionally related disorder.

In another aspect, the presently disclosed and/or claimed inventive concept(s) provides a method of preventing or treating a nutritionally related disorder, comprising administering a range of food products according to the presently disclosed and/or claimed inventive concept(s).

The nutritionally related disease is optionally selected from obesity, malnutrition, diabetes and heart disease.

Other and further objects, features, and advantages of the presently disclosed and/or claimed inventive concept(s) will be readily apparent to those skilled in the art.

In one aspect, the presently disclosed and/or claimed inventive concept(s) provides a range of infant food products wherein each product in the range has less than about 15 micrograms furan per kilogram of food product. In view of the fact that furan concentrations can be used as a good indicator of undesirable by-products formed during processing, a range of food products according to the presently disclosed and/or claimed inventive concept(s) has the advantage that each food product in the range has low levels of undesirable by products.

In a particular, non-limiting embodiment, each product in the range comprises less than about 20 micrograms furan per kilogram of food product. For example (but not by way of limitation), each product in the range comprises less than about 10 micrograms furan per kilogram of food product. In another non-limiting example, each product in the range comprises less than about 5 micrograms furan per kilogram of food product. In yet another non-limiting example, each product in the range comprises less than about 2 micrograms furan per kilogram of food product.

In a particular, non-limiting embodiment, the components include substantially no furan (e.g. less than 1 micrograms furan per kilogram of food product) or no measurable furan.

In certain non-limiting embodiments, the range of products comprises at least one food product suitable for each stage of infant development.

In certain non-limiting embodiments, the range of products comprises two or more food products suitable for each stage of infant development. In certain other non-limiting embodiments, the range of products comprises at least a vegetable based product and a fruit based product for each stage of infant development. In certain other non-limiting embodiments, the range of products comprises a plurality of vegetable based products and fruit based products for each stage of infant development.

In certain non-limiting embodiments, the range of products comprises at least a vegetable based product and a fruit based product for stage 1 of infant development.

In certain non-limiting embodiments, the range of products comprises at least a vegetable based product, a complete meal and a fruit based product for stage 2 of infant development. A complete meal is designed to provide one nutritionally balanced serving—it is not necessary to combine the complete meal with another food product to provide a meal.

In certain non-limiting embodiments, the range of products comprises at least a vegetable based product, a complete meal and a fruit based product for stage 3 of infant development.

In certain non-limiting embodiments, the range of products comprises at least a vegetable based product, a complete meal and a fruit based product for stage 4 of infant development.

In certain non-limiting embodiments, the infant food products for infants from about 4 to about 6 months of age (Stage 1) comprise one or more vegetables selected from artichoke, carrot, cucumber, fennel, French bean, leek, lettuce, parsnip, potato, pumpkin, squash and zucchini.

In certain non-limiting embodiments, infant food products for infants from about 4 to about 6 months of age (Stage 1) comprise the legume soy.

In certain non-limiting embodiments, infant food products for infants from about 4 to about 6 months of age (Stage 1) comprise one or more meats selected from beef, veal, chicken, lamb, pork, turkey and duck.

In certain non-limiting embodiments, infant food products for infants from about 4 to about 6 months of age (Stage 1) comprise one or more fruits selected from apple, apricot, banana, blackberry, blackcurrant, bilberry, cherry, date, grape, gooseberry, guava, lemon, lime, mandarin, mango, melon, nectarine, olive, orange, peach, pear, pineapple, plum, quince, raspberry, redcurrant and watermelon.

In certain non-limiting embodiments, infant food products for infants from about 4 to about 6 months of age (Stage 1) comprise one or more aromatic herbs and spices selected from anise, balm mint, chamomile, caraway, gherkin, orange blossom and sorrel.

In certain non-limiting embodiments, infant food products for infants from about 6 to about 8 months of age (Stage 2) comprise one or more vegetables selected from artichoke, carrot, cucumber, fennel, French bean, leek, lettuce, parsnip, potato, pumpkin, squash, zucchini, broccoli, cauliflower, eggplant (aubergine), sweet potato, tomato, pea and spinach.

In certain non-limiting embodiments, infant food products for infants from about 6 to about 8 months of age (Stage 2) comprise one or more legumes selected from soy, black gram seed, chickpea, cowpea, kidney bean, lentil, mung bean and pigeon pea.

In another embodiment, infant food products for infants from about 6 to about 8 months of age (Stage 2) comprise one or more meats selected from of beef, veal, chicken, lamb, pork, turkey and duck, and/or fish.

In certain non-limiting embodiments, infant food products for infants from about 6 to about 8 months of age (Stage 2) comprise one or more fruits selected from apple, apricot, banana, blackberry, blackcurrant, bilberry, cherry, date, grape, gooseberry, guava, lemon, lime, mandarin, mango, melon, nectarine, olive, orange, peach, pear, pineapple, plum, quince, raspberry, redcurrant, watermelon, fig, papaya, passionfruit, strawberry and tangerine.

In certain non-limiting embodiments, infant food products for infants from about 6 to about 8 months of age (Stage 2) comprise one or more aromatic herbs and spices selected from anise, balm mint, chamomile, caraway, gherkin, orange blossom, sorrel, cardamom, chives, cumin, onion, saffron, savory, shallot and thyme.

In certain non-limiting embodiments, infant food products for infants from about 6 to about 8 months of age (Stage 2) comprise coconut.

In certain non-limiting embodiments, infant food products for infants from about 8 to about 12 months of age (Stage 3) comprise one or more vegetables selected from artichoke, carrot, cucumber, fennel, French bean, leek, lettuce, parsnip, potato, pumpkin, squash, zucchini, broccoli, cauliflower, eggplant (aubergine), sweet potato, tomato, pea, spinach, asparagus, beet(root), brussel sprout, cabbage, garden pea, radish and turnip.

In certain non-limiting embodiments, infant food products for infants from about 8 to about 12 months of age (Stage 3) comprise one or more legumes selected from soy, black gram seed, chickpea, cowpea, kidney bean, lentil, mung bean, pigeon pea, lima bean and winged bean.

In certain non-limiting embodiments, infant food products for infants from about 8 to about 12 months of age (Stage 3) comprise one or more meats selected from beef, veal, chicken, lamb, pork, turkey and duck, and/or fish and/or eggs.

In certain non-limiting embodiments, infant food products for infants from about 8 to about 12 months of age (Stage 3) comprise one or more fruits selected from apple, apricot, banana, blackberry, blackcurrant, bilberry, cherry, date, grape, gooseberry, guava, lemon, lime, mandarin, mango, melon, nectarine, olive, orange, peach, pear, pineapple, plum, quince, raspberry, redcurrant, watermelon, fig, papaya, passionfruit, strawberry, tangerine and rhubarb.

In certain non-limiting embodiments, infant food products for infants from about 8 to about 12 months of age (Stage 3) comprise one or more aromatic herbs and spices selected from anise, balm mint, chamomile, caraway, gherkin, orange blossom, sorrel, cardamom, chives, cumin, onion, saffron, savory, shallot, thyme, coriander, curcuma, garden sorrel, garlic, mint and vanilla.

In certain non-limiting embodiments, infant food products for infants from about 8 to about 12 months of age (Stage 3) comprise coconut and/or cocoa.

In certain non-limiting embodiments, it may be desired that infant food products for infants from about 12 to about 36 months of age (Stage Junior) comprise one or more vegetables selected from artichoke, carrot, cucumber, fennel, French bean, leek, lettuce, parsnip, potato, pumpkin, squash, zucchini, broccoli, cauliflower, eggplant (aubergine), sweet potato, tomato, pea, spinach, asparagus, beet (root), brussel sprout, cabbage, garden pea, radish, turnip, mushroom and watercress.

In certain non-limiting embodiments, infant food products for infants from about 12 to about 36 months of age (Stage Junior) comprise one or more legumes selected from soy, black gram seed, chickpea, cowpea, kidney bean, lentil, mung bean, pigeon pea, lima bean and winged bean.

In certain non-limiting embodiments, infant food products for infants from about 12 to about 36 months of age (Stage Junior) comprise one or more meats selected from beef, veal, chicken, lamb, pork, turkey, duck, and/or fish, and/or eggs and/or crustaceans.

In certain non-limiting embodiments, infant food products for infants from about 12 to about 36 months of age (Stage Junior) comprise one or more fruits selected from apple, apricot, banana, blackberry, blackcurrant, bilberry, cherry, date, grape, gooseberry, guava, lemon, lime, mandarin, mango, melon, nectarine, olive, orange, peach, pear, pineapple, plum, quince, raspberry, redcurrant, watermelon, fig, papaya, passionfruit, strawberry, tangerine, rhubarb, grapefruit and kiwi.

In certain non-limiting embodiments, infant food products for infants from about 12 to about 36 months of age (Stage Junior) comprise one or more aromatic herbs and spices selected from anise, balm mint, chamomile, caraway, gherkin, orange blossom, sorrel, cardamom, chives, cumin, onion, saffron, savory, shallot, thyme, coriander, curcuma, garden sorrel, garlic, mint, vanilla, basil, bay laurel, chervil, cinnamon, clove, ginger, liquorice, mace, marjoram, nutmeg, oregano, parsley, pepper, rosemary, sage and tarragon.

In certain non-limiting embodiments, infant food products for infants from about 12 to about 36 months of age (Stage Junior) comprise one or more nuts selected from coconut, cocoa, almond, beechnut, brazil nut, cashew nut, chestnut, hazelnut, macadamia nut, pecan nut, pistachio nut and walnut.

In a further aspect, the presently disclosed and/or claimed inventive concept(s) provides a method for production of the food product which comprises precooking the ingredients separately, mixing the ingredients, subjecting them to UHT treatment and aseptically filling packaging containers. Advantageously, it has been found that food products of the presently disclosed and/or claimed inventive concept(s) produced in this way have reduced levels of by-products including furan compared to similar products processed using conventional retorting.

In a further aspect, the presently disclosed and/or claimed inventive concept(s) provides a feeding regime for meeting the nutritional needs of an infant during different stages of development, the regime comprising administering to an infant a range of food products according to the presently disclosed and/or claimed inventive concept(s).

In a further aspect, the presently disclosed and/or claimed inventive concept(s) provides use of a range of food products according to the presently disclosed and/or claimed inventive concept(s) in the manufacture of one or more medicaments for the prevention or treatment of a nutritionally related disorder.

In another aspect, the presently disclosed and/or claimed inventive concept(s) provides a method of preventing or treating a nutritionally related disorder, comprising administering a range of food products according to the presently disclosed and/or claimed inventive concept(s).

The nutritionally related disease is optionally selected from obesity, malnutrition, diabetes and heart disease.

In other aspects, the presently disclosed and/or claimed inventive concept(s) provides the product produced using the method of the presently disclosed and/or claimed inventive concept(s).

EXAMPLES

This presently disclosed and/or claimed inventive concept(s) can be further illustrated by the following examples although it will be understood that these examples are included merely for purposes of illustration and are not intended to limit the scope of the presently disclosed and/or claimed inventive concept(s) unless otherwise specifically indicated.

Example Products

A daily complementary diet for stage 1 comprised:
(i) 100 g portion of infant cereal;
(ii) 65 g portion of vegetable dish in accordance with the presently disclosed and/or claimed inventive concept(s); and
(iii) 65 g portion of fruit dish in accordance with the presently disclosed and/or claimed inventive concept(s).

Figure 1:
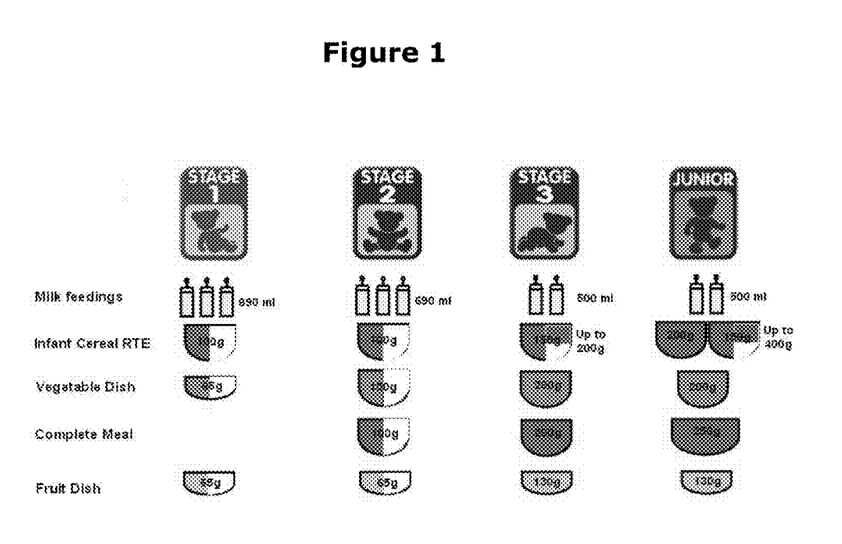
FIG. 1 illustrates a feeding plan according to the presently disclosed and/or claimed inventive concept(s).

A number of vegetable and fruit dishes were provided in a range of baby food products and were labeled according to their suitability for a stage 1 diet. The feeding plan shown in FIG. 1 was used to determine which meals could make up the daily food intake for stage 1. In this example, the vegetable dish was a pumpkin based dish and the fruit dish was an apple based dish.

TABLE 1

List of ingredients for vegetable dish

| Ingredient | Amount per 100 g (g) |
| --- | --- |
| POTATO FLAKES | 4.000 |
| Pumpkin frozen | 40.000 |
| Potato 6 × 6 mm frozen | 10.000 |
| CARROT | 15.000 |
| RAPESEED OIL LOW ERUCIC (CANOLA) | 0.400 |
| SUNFLOWER OIL | 0.400 |
| WATER | 30.200 |

TABLE 2

List of ingredients for fruit dish

| Ingredient | Amount per 100 g (g) |
| --- | --- |
| Apple fresh | 99.95 |
| Vitamin C | 0.05 |

Each dish provided the following nutritional values:

TABLE 3

Nutritional values provided by each Stage 1 dish

| | kcal/100 g | kcal/serving | % daily energy intake |
| --- | --- | --- | --- |
| Cereal Dish | 106.0 for RTE pap 424 for dry powder | 106.00 | 17.0 |
| Vegetable Dish | 40.7 | 26.46 | 4.2 |
| Fruit Dish | 53.2 | 34.58 | 5.5 |

The total daily nutritional values provided by the complementary dishes were as follows:

TABLE 4

Daily nutritional values provided by the Stage 1 complementary dishes

| | per day | per 100 g | E % (daily energy intake) |
| --- | --- | --- | --- |
| Total Protein (g) | 4.3 | 2.8 | 10.4 |
| Total Fat (g) | 3.3 | 2.2 | 18.1 |

TABLE 4-continued

Daily nutritional values provided by the Stage 1 complementary dishes

| | per day | per 100 g | E % (daily energy intake) |
| --- | --- | --- | --- |
| Total CHO (g) | 29.8 | 19.2 | 71.5 |
| Fibres (g) | 3.1 | 2.0 | — |
| Sodium (mg) | 38.1 | 24.6 | — |
| LA (g) | 0.8 | 0.5 | 4.3 |
| ALA (g) | 0.1 | 0.1 | 0.6 |
| LA/ALA ratio | 7.1 | — | — |
| Energy (kcal) | 166.5 | 107.4 | — |

(Wherein CHO represents carbohydrate, LA represents linoleic acid and ALA represents alpha-linolenic acid).

The sum of the daily energy intake provided by the complementary foods was 26.6% (166.5 kcal). The remaining 73.4% (458 kcal) of daily energy intake was provided by milk. This provided a total daily energy intake of 625.04 kcal.

Example 2

A daily complementary diet for stage 2 comprised:
(i) 100 g portion of infant cereal;
(ii) 100 g portion of vegetable dish in accordance with the presently disclosed and/or claimed inventive concept(s);
(iii) 100 g portion of a complete meal in accordance with the presently disclosed and/or claimed inventive concept(s); and
(iv) 65 g portion of fruit dish in accordance with the presently disclosed and/or claimed inventive concept(s).

A number of complete meals, vegetable and fruit dishes were provided in the range of baby food products and were labeled according to their suitability for a stage 2 diet. The feeding plan shown in FIG. 1 was used to determine which meals could make up the daily food intake for stage 2. In this example, the vegetable dish was garden vegetables and corn based, the complete meal was garden vegetables and lamb based and the fruit dish was apple and raspberry based.

TABLE 5

List of ingredients for vegetable dish

| Ingredient | Amount per 100 g (g) |
| --- | --- |
| CARROT | 30.000 |
| POTATO FLAKES | 3.000 |
| Sweetcorn frozen | 10.000 |
| Parsnip frozen | 10.000 |
| RICE SEMOLINA | 1.000 |
| RAPESEED OIL LOW ERUCIC (CANOLA) | 0.400 |
| Fennel frozen | 5.000 |
| SUNFLOWER OIL | 0.200 |
| WATER | 40.400 |

TABLE 6

List of ingredients for complete meal

| Ingredient | Amount per 100 g (g) |
| --- | --- |
| POTATO FLAKES | 4.000 |
| CARROT | 30.000 |

TABLE 6-continued

List of ingredients for complete meal

| Ingredient | Amount per 100 g (g) |
|---|---|
| Lamb frozen | 8.500 |
| RICE SEMOLINA | 2.000 |
| Parsnip frozen | 5.000 |
| Sweetcorn frozen | 3.000 |
| RAPESEED OIL LOW ERUCIC (CANOLA) | 0.600 |
| SUNFLOWER OIL | 0.400 |
| Onion 10 mm frozen | 4.000 |
| WATER | 42.500 |

TABLE 7

List of ingredients for fruit dish

| Ingredient | Amount per 100 g (g) |
|---|---|
| Apple fresh | 79.96 |
| Raspberry puree | 19.99 |
| Vitamin C | 0.05 |

Each dish provided the following nutritional values:

TABLE 8

Nutritional values provided by each Stage 2 dish

|  | kcal/100 g | kcal/serving | % daily energy intake |
|---|---|---|---|
| Cereal Dish | 106.0 for RTE pap 424 for dry powder | 106.00 | 15.8 |
| Vegetable Dish | 42.6 | 42.6 | 6.4 |
| Complete Meal | 62.6 | 62.6 | 9.3 |
| Fruit Dish | 50.2 | 32.63 | 4.9 |

The total daily nutritional values provided by the complementary dishes were as follows:

TABLE 9

Daily nutritional values provided by the Stage 2 complementary dishes

|  | per day | per 100 g | E % (daily energy intake) |
|---|---|---|---|
| Total Protein (g) | 7.8 | 2.7 | 12.9 |
| Total Fat (g) | 6.2 | 2.1 | 23.1 |
| Total CHO (g) | 38.5 | 13.3 | 63.9 |
| Fibres (g) | 5.2 | 1.8 | — |
| Sodium (mg) | 75.7 | 26.1 | — |
| LA (g) | 1.2 | 0.4 | 4.6 |
| ALA (g) | 0.2 | 0.1 | 0.6 |
| LA/ALA ratio | 7.3 | — | — |
| Energy (kcal) | 241.1 | 83.1 | — |

The sum of the daily energy intake provided by the complementary foods was 35.9% (241.1 kcal). The remaining 64.1% (428.93 kcal) of daily energy intake was provided by milk. This provided a total daily energy intake of 670.03 kcal.

Example 3

A daily complementary diet for stage 3 comprised:
(i) 150 g portion of infant cereal;
(ii) 200 g portion of vegetable dish in accordance with the presently disclosed and/or claimed inventive concept(s);
(iii) 200 g portion of a complete meal in accordance with the presently disclosed and/or claimed inventive concept(s); and
(iv) 130 g portion of fruit dish in accordance with the presently disclosed and/or claimed inventive concept(s).

A number of complete meal, vegetable and fruit dishes were provided in the range of baby food products and were labeled according to their suitability for a stage 3 diet. The feeding plan shown in FIG. 1 was used to determine which meals could make up the daily food intake for stage 3. In this example, vegetable dish was garden vegetables and corn based, the complete meal was a pasta, tomato and beef based and the fruit dish was fruit salad based.

TABLE 10

List of ingredients for vegetable dish

| Ingredient | Amount per 100 g (g) |
|---|---|
| CARROT | 30.000 |
| POTATO FLAKES | 3.000 |
| Sweetcorn frozen | 10.000 |
| Parsnip frozen | 10.000 |
| RICE SEMOLINA | 1.000 |
| RAPESEED OIL LOW ERUCIC (CANOLA) | 0.400 |
| Fennel frozen | 5.000 |
| SUNFLOWER OIL | 0.200 |
| WATER | 40.400 |

TABLE 11

List of ingredients for complete meal

| Ingredient | Amount per 100 g (g) |
|---|---|
| Pasta spaghetti short | 8.000 |
| Beef frozen 14% fat | 8.000 |
| CARROT | 20.000 |
| Tomato puree | 5.000 |
| RAPESEED OIL LOW ERUCIC (CANOLA) | 0.800 |
| SUNFLOWER OIL | 0.400 |
| Bell pepper red 10 mm frozen | 4.000 |
| Onion 10 mm frozen | 3.000 |
| Thyme frozen | 0.100 |
| WATER | 50.700 |

TABLE 12

List of ingredients for fruit dish

| Ingredient | Amount per 100 g (g) |
|---|---|
| Apple fresh | 39.98 |
| Pear William fresh | 14.9925 |
| Peach puree | 14.9925 |
| Banana puree without seeds | 19.990 |
| Apricot puree | 9.995 |
| Vitamin C | 0.05 |

Each dish provided the following nutritional values:

TABLE 13

Nutritional values provided by each Stage 3 dish

|  | Kcal/100 g | kcal/serving | % daily energy intake |
|---|---|---|---|
| Cereal Dish | 106.0 | 159.00 | 20.6 |
| Vegetable Dish | 42.6 | 85.2 | 11.1 |

TABLE 13-continued

Nutritional values provided by each Stage 3 dish

|  | Kcal/100 g | kcal/serving | % daily energy intake |
|---|---|---|---|
| Complete Meal | 65.9 | 131.8 | 17.1 |
| Fruit Dish | 56.0 | 72.8 | 9.5 |

The total daily nutritional values provided by the complementary dishes were as follows:

TABLE 14

Daily nutritional values provided by the Stage 3 complementary dishes

|  | Per day | per 100 g | E % |
|---|---|---|---|
| Total Protein (g) | 14.8 | 2.6 | 13.2 |
| Total Fat (g) | 10.9 | 1.9 | 22 |
| Total CHO (g) | 72.4 | 12.8 | 64.8 |
| Fibres (g) | 8.4 | 1.5 | — |
| Sodium (mg) | 142.3 | 25.1 | — |
| LA (g) | 2.3 | 0.4 | 4.6 |
| ALA (g) | 0.4 | 0.1 | 0.7 |
| LA/ALA ratio | 6.5 | — | — |
| Energy (kcal) | 447.0 | 78.8 | — |

The sum of the daily energy intake provided by the complementary foods was 58.0% (447.0 kcal). The remaining 42.0% (323.0 kcal) of daily energy intake was provided by milk. This provided a total daily energy intake of 770 kcal.

Example 4

A daily complementary diet for stage 4 comprised:
(i) 350 g portion of infant cereal;
(ii) 200 g portion of vegetable dish in accordance with the presently disclosed and/or claimed inventive concept(s);
(iii) 250 g portion of a complete meal in accordance with the presently disclosed and/or claimed inventive concept(s); and
(iv) 130 g portion of fruit dish in accordance with the presently disclosed and/or claimed inventive concept(s).

A number of complete meals, vegetable and fruit dishes were provided in the range of baby food products and were labeled according to their suitability for a stage 4 diet. The feeding plan shown in FIG. 1 was used to determine which meals could make up the daily food intake for stage 4. In this example, the vegetable dish was a garden vegetables and corn dish, the complete meal was a pasta, tomato and beef dish and the fruit dish was a fruit salad dish.

TABLE 15

List of ingredients for vegetable dish

| Ingredient | Amount per 100 g (g) |
|---|---|
| CARROT | 30.000 |
| POTATO FLAKES | 3.000 |
| Sweetcorn frozen | 10.000 |
| Parsnip frozen | 10.000 |
| RICE SEMOLINA | 1.000 |
| RAPESEED OIL LOW ERUCIC (CANOLA) | 0.400 |
| Fennel frozen | 5.000 |

TABLE 15-continued

List of ingredients for vegetable dish

| Ingredient | Amount per 100 g (g) |
|---|---|
| SUNFLOWER OIL | 0.200 |
| WATER | 40.400 |

TABLE 16

List of ingredients for complete meal

| Ingredient | Amount per 100 g (g) |
|---|---|
| Pasta spaghetti short | 8.000 |
| Beef frozen 14% fat | 8.000 |
| CARROT | 20.000 |
| Tomato puree | 5.000 |
| RAPESEED OIL LOW ERUCIC (CANOLA) | 0.800 |
| SUNFLOWER OIL | 0.400 |
| Bell pepper red 10 mm frozen | 4.000 |
| Onion 10 mm frozen | 3.000 |
| Thyme frozen | 0.100 |
| WATER | 50.700 |

TABLE 17

List of ingredients for fruit dish

| Ingredient | Amount per 100 g (g) |
|---|---|
| Apple fresh | 39.98 |
| Pear William fresh | 14.9925 |
| Peach puree | 14.9925 |
| Banana puree without seeds | 19.990 |
| Apricot puree | 9.995 |
| Vitamin C | 0.05 |

Each dish provided the following nutritional values:

TABLE 18

Nutritional values provided by each Stage 4 dish

|  | kcal/100 g | kcal/serving | % daily energy intake |
|---|---|---|---|
| Cereal Dish | 106.0 | 371 | 35.7 |
| Vegetable Dish | 42.6 | 85.2 | 8.2 |
| Complete Meal | 65.9 | 164.75 | 15.8 |
| Fruit Dish | 56.0 | 72.8 | 7.0 |

The daily nutritional values provided by the complementary dishes were as follows:

TABLE 19

Daily nutritional values provided by the Stage 4 complementary dishes

|  | per day | per 100 g | E % |
|---|---|---|---|
| Total Protein (g) | 23.6 | 3.5 | 13.6 |
| Total Fat (g) | 17.2 | 2.6 | 22.4 |
| Total CHO (g) | 110.6 | 16.6 | 64.0 |
| Fibres (g) | 9.8 | 1.5 | — |
| Sodium (mg) | 215.0 | 32.2 | — |
| LA (g) | 3.4 | 0.5 | 4.5 |
| ALA (g) | 0.5 | 0.1 | 0.7 |
| LA/ALA ratio | 6.8 | — | — |
| Energy (kcal) | 691.7 | 103.6 | — |

The sum of the daily energy intake provided by the complementary foods was 66.5% (691.7 kcal). The remaining 33.5% (348.3 kcal) of daily energy intake was provided by milk. This provided a total daily energy intake of 1040 kcal.

Test Results and Data

Figure 2:
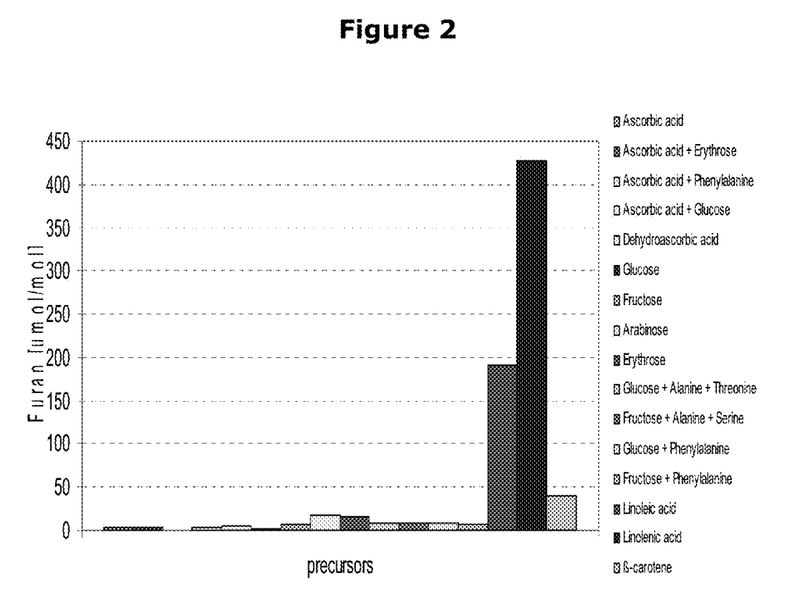
FIGS. 2 and 3 illustrate the results of studies to investigate furan formation in aqueous model systems at pH 7 and pH 4, respectively, following heat treatment at 121° C. for 25 minutes.
Figure 3:
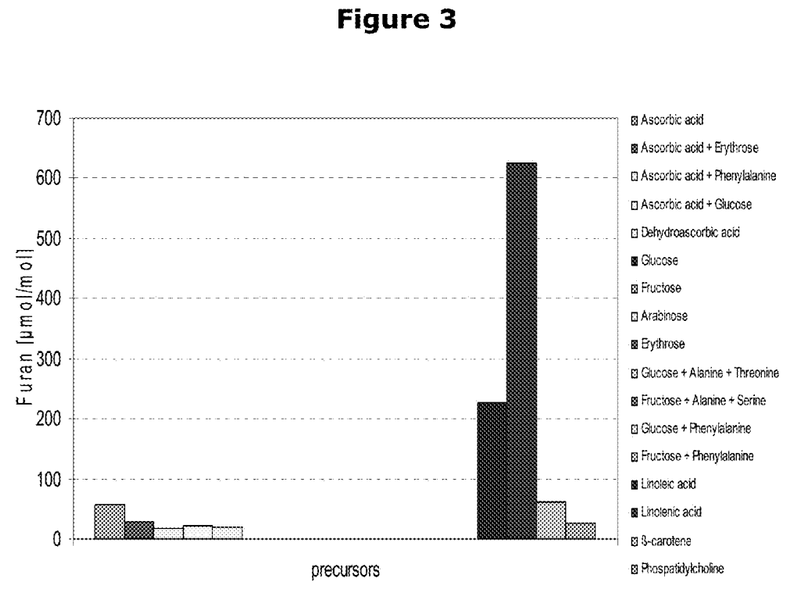

Furan formation was studied in aqueous model systems at pH 7 and pH 4 following heat treatment at 121° C. for 25 minutes. The results are shown in FIGS. 2 and 3. The results show that at pH 7, the concentration of PUFAs show the highest impact on furan development after heat treatment at 121° C. for 25 minutes.

At pH 4, ascorbic acid plays an important role as a precursor of furan after heat treatment at 121° C. for 25 minutes, but it can be seen that PUFAs still show the highest impact on furan development.

Figure 4:
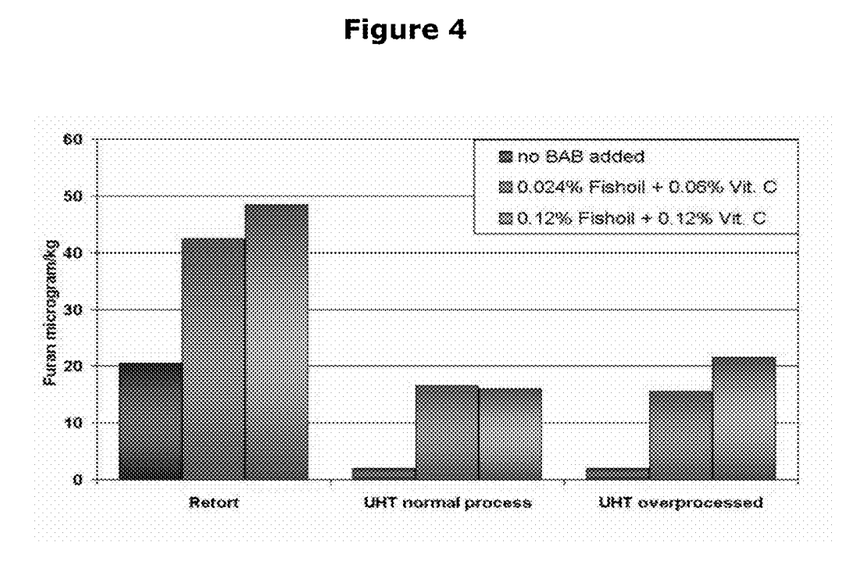
FIG. 4 illustrates the results of a study carried out to investigate the amount of furan formation relative to the addition of ascorbic acid and LC-PUFA derived from fish oil.
Figure 5:
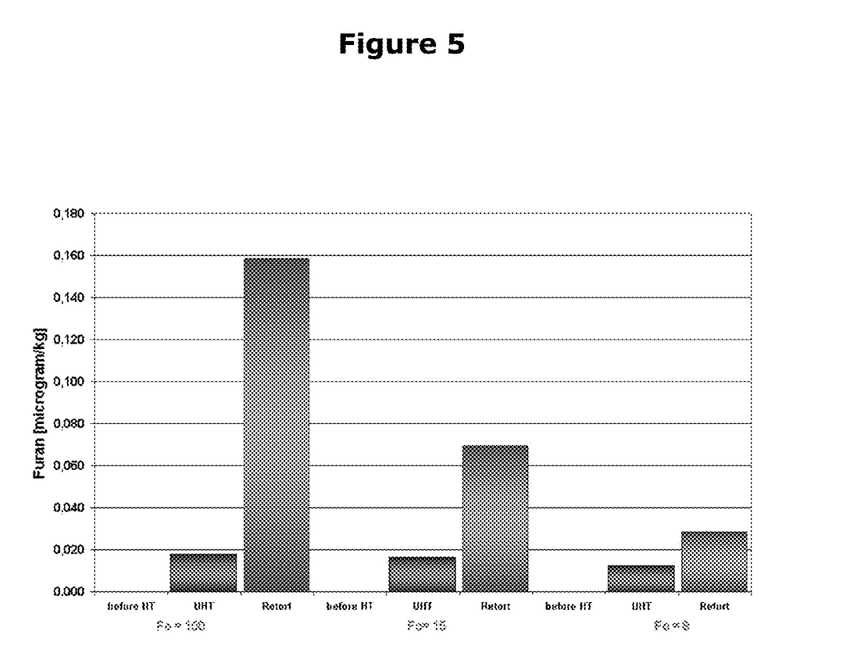
FIGS. 5 and 6 illustrate the results of a study carried out to investigate the concentration of furan formation relative to the sterilization conditions used for processing of the food product.
Figure 6:
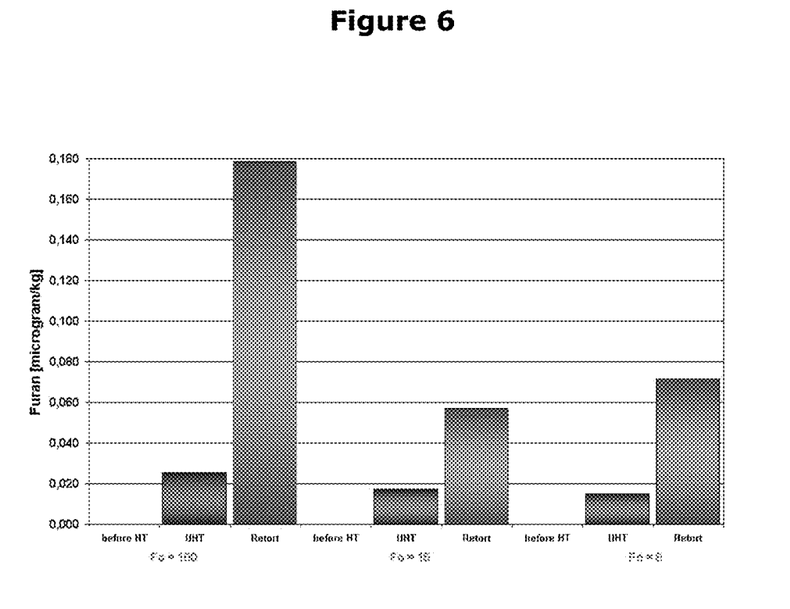

Two further studies were carried out. The first study was carried out to investigate the amount of furan formation relative to the addition of ascorbic acid and LC-PUFA derived from fish oil and the results are shown in FIG. 4. The second study was carried out to investigate the concentration of furan formation relative to the sterilization conditions used for processing of the food product and the results are shown in FIGS. 5 and 6. In FIG. 5 the results are shown with regard to a vegetable food product comprising carrot. In FIG. 6 the results are shown with regard to a savoury food product comprising cod and mixed vegetables. It can be seen that there is about 2 micrograms of furan per kg food product produced as a by-product following processing according to the presently disclosed and/or claimed inventive concept(s).

The results clearly show that increased levels of fish oil and vitamin C lead to larger levels of furan production. In addition, sterilization of the food product by retorting lead to remarkably larger levels of furan production in the food product compared to sterilization by UHT treatment at F0=100, F0=15 and F0=8. (F0 is a well known indicator of sterility—the F0 value is a known measure of the time required to kill *clostridium botulinum* bacteria). Indeed, it can clearly be seen that UHT sterilization minimizes the formation of furan by a factor of 2.5 to 5 compared to traditional retorting under normal sterilization conditions. In addition, remarkably, while amplified sterilization conditions resulted in a linear increase of Furan formation in products processed by retorting, furan formation as a result of UHT treatment remained almost constant.

In the specification, there have been disclosed typical particular non-limiting embodiments of the presently disclosed and/or claimed inventive concept(s) and, although specific terms are employed, they are used in a generic and descriptive sense only and not for purposes of limitation, the scope of the presently disclosed and/or claimed inventive concept(s) being set forth in the following claims. Obviously many modifications and variations of the presently disclosed and/or claimed inventive concept(s) are possible in light of the above teachings. It is therefore to be understood that within the scope of the appended claims the presently disclosed and/or claimed inventive concept(s) may be practiced otherwise than as specifically described.

What is claimed is:

1. A method of producing a heat processed, aseptically packaged infant food product from a plurality of ingredients, the method comprising the steps of:
   precooking the plurality of ingredients separately;
   mixing the precooked ingredients;
   subjecting the mixed, precooked ingredients to ultra-high-temperature (UHT) sterilization;
   aseptically packaging the UHT-treated infant food product within a packaging container following UHT sterilization; and
   wherein the heat processed, aseptically packaged infant food product has reduced levels of furan produced during processing when compared to similar products processed using conventional retorting under sterilization conditions, as indicated by less than about 5 micrograms furan per kg food product.

2. The method of claim 1, wherein the heat processed, aseptically packaged infant food product contains less than about 2 micrograms furan per kg infant food product.

3. The method of claim 1, wherein the heat processed, aseptically packaged infant food product contains substantially no furan.

4. The method of claim 1, wherein the heat processed, aseptically packaged infant food product contains no added fish oil.

5. The method of claim 1, wherein the heat processed, aseptically packaged infant food product contains no added vitamin C.

6. A method of producing a plurality of heat processed, aseptically packaged infant food products, each of the plurality of heat processed, aseptically packaged infant food products comprising a plurality of ingredients and being produced by the method comprising the steps of:
   precooking the plurality of ingredients separately;
   mixing the precooked ingredients;
   subjecting the mixed, precooked ingredients to ultra-high-temperature (UHT) sterilization;
   aseptically packaging the UHT-treated infant food product within a packaging container following UHT sterilization; and
   wherein each of the plurality of heat processed, aseptically packaged infant food products have reduced levels of furan produced during processing when compared to similar products processed using conventional retorting under sterilization conditions, as indicated by less than about 5 micrograms furan per kg food product.

7. The method of claim 6, wherein each of the plurality of heat processed, aseptically packaged infant food product contains less than about 2 micrograms furan per kg infant food product.

8. The method of claim 6, wherein each of the plurality of heat processed, aseptically packaged infant food product contains substantially no furan.

9. The method of claim 6, wherein the plurality of heat processed, aseptically packaged infant food products comprises two or more heat processed, aseptically packaged infant food products suitable for two or more stages of infant development.

10. The method of claim 6, wherein the plurality of heat processed, aseptically packaged infant food products comprises at least one vegetable based product and at least one fruit based product for one or more stages of infant development.

11. The method of claim 6, wherein the plurality of heat processed, aseptically packaged infant food products comprises a plurality of vegetable based products and a plurality of fruit based products for one or more stages of infant development.

12. The method of claim 6, wherein the plurality of heat processed, aseptically packaged infant food products comprises at least one vegetable based product and at least one fruit based product for stage 1 of infant development, wherein stage 1 of infant development comprises from about 4 months to about 6 months of age.

13. The method of claim 6, wherein the plurality of heat processed, aseptically packaged infant food products comprises at least one vegetable based product, at least one meat based product, and at least one fruit based product for stage 2 of infant development, wherein stage 2 of infant development comprises from about 6 months to about 8 months of age.

14. The method of claim 6, wherein the plurality of heat processed, aseptically packaged infant food products comprises at least one vegetable based product, at least one meat based product, and at least one fruit based product for stage 3 of infant development, wherein stage 3 of infant development comprises from about 8 months to about 12 months of age.

15. The method of claim 6, wherein the plurality of heat processed, aseptically packaged infant food products comprises at least one vegetable based product, at least one meat based product, and at least one fruit based product for stage 4 of infant development, wherein stage 4 of infant development comprises from about 12 months to about 36 months of age.

16. The method of claim 6, wherein the plurality of heat processed, aseptically packaged infant food products comprises at least eight heat processed, aseptically packaged infant food products that include:
   (i) at least one vegetable based product and at least one fruit based product for stage 1 of infant development;
   (ii) at least one vegetable based product and at least one fruit based product for stage 2 of infant development;
   (iii) at least one vegetable based product and at least one fruit based product for stage 3 of infant development; and
   (iv) at least one vegetable based product and at least one fruit based product for stage 4 of infant development.

17. The method of claim 16, further comprising at least three additional heat processed, aseptically packaged infant food products in addition to the at least eight heat processed, aseptically packaged infant food products of (i)-(iv), wherein each of the at least three additional heat processed, aseptically packaged infant food products is produced by the same method and thus contain less than about 5 micrograms furan per kg food product, and wherein the at least three additional heat processed, aseptically packaged infant food products comprise at least one meat based product for each of stages 2-4 of infant development.

* * * * *